United States Patent
Hou

(10) Patent No.: US 6,322,521 B1
(45) Date of Patent: Nov. 27, 2001

(54) METHOD AND SYSTEM FOR ON-LINE HEARING EXAMINATION AND CORRECTION

(75) Inventor: Zezhang Hou, Cupertino, CA (US)

(73) Assignee: Audia Technology, Inc., Cupertino, CA (US)

( * ) Notice: Subject to any disclaimer, the term of this patent is extended or adjusted under 35 U.S.C. 154(b) by 0 days.

(21) Appl. No.: 09/541,366

(22) Filed: Mar. 31, 2000

Related U.S. Application Data

(60) Provisional application No. 60/189,010, filed on Mar. 13, 2000, and provisional application No. 60/177,695, filed on Jan. 24, 2000.

(51) Int. Cl.$^7$ ........................................... A61B 5/00
(52) U.S. Cl. ........................................... 600/559; 381/23.1
(58) Field of Search ........................................... 600/300, 552, 600/559; 381/1–433

(56) References Cited

U.S. PATENT DOCUMENTS

| 3,974,335 | | 8/1976 | Blackledge . | |
|---|---|---|---|---|
| 4,320,256 | | 3/1982 | Freeman . | |
| 4,964,304 | | 10/1990 | Eckstein . | |
| 5,226,086 | * | 7/1993 | Platt | 381/58 |
| 5,303,306 | | 4/1994 | Brillhart et al. . | |
| 5,729,658 | | 3/1998 | Hou et al. . | |
| 5,811,681 | | 9/1998 | Braun et al. . | |
| 5,991,417 | * | 11/1999 | Topholm | 381/60 |
| 6,061,431 | * | 5/2000 | Knapp et al. | 379/52 |
| 6,086,541 | * | 7/2000 | Rho | 600/559 |

* cited by examiner

*Primary Examiner*—John P. Lacyk
*Assistant Examiner*—Pamela Wingood
(74) *Attorney, Agent, or Firm*—Beyer Weaver & Thomas, LLP

(57) ABSTRACT

Improved approaches to assist those having hearing loss are disclosed. One approach pertains to providing on-line hearing loss testing. The on-line hearing loss testing can be self-performed without any specialized equipment. Another approach pertains to on-line sound customization. The sound customization can simulate hearing compensation on-line. As an example, the hearing compensation can be used to simulate hearing aid processing. Still another approach pertains to a recommendation and/or referral procedure.

45 Claims, 13 Drawing Sheets

FIG. 7

METHOD AND SYSTEM FOR ON-LINE HEARING EXAMINATION AND CORRECTION

CROSS-REFERENCE TO RELATED APPLICATIONS

This application claims the benefit of: (i) U.S. Provisional Application No. 60/177,695, filed Jan. 24, 2000, and entitled "REMOTE HEARING TEST", the contents of which is hereby incorporated by reference; and (ii) U.S. Provisional Application No. 60/189,010, filed Mar. 13, 2000, and entitled "METHOD AND SYSTEM FOR ON-LINE HEARING EXAMINATION AND CORRECTION", the contents of which is hereby incorporated by reference. This application is also related to U.S. application Ser. No. 09/540,577, filed concurrently herewith, and entitled "METHOD AND SYSTEM FOR ON-LINE HEARING EXAMINATION USING CALIBRATED LOCAL MACHINE", the contents of which is hereby incorporated by reference.

BACKGROUND OF THE INVENTION

1. Field of the Invention

The present invention relates to hearing loss and, more particularly, to hearing loss evaluation and correction assistance.

2. Description of the Related Art

One out of ten people suffer from some degree of hearing loss. However, due to stigma, cost, and availability only about 25% of those who have hearing loss wear hearing aids. Many people do not want to wear hearing aids because they view hearing aids as a symbol of disability. In many countries (including the United States) hearing specialists, such as audiologists, perform hearing loss diagnosis. The diagnosis and subsequent fitting of a hearing aid device is a costly process. In developing countries, hearing specialists are rare and thus people of developing counties are often unable to get assistance. There are also many people with impaired hearing that are not aware that they have impaired hearing. Many people in this category are reluctant to spend the time and money to have their hearing examined by a hearing specialist.

More particularly, in most developed countries, hearing loss is diagnosed using specialized equipment known as an audiometer. Typically, a patient must visit a hearing specialists office or an ear, noise and throat (ENT) doctor's office to have hearing loss testing performed. If hearing loss is diagnosed, the hearing specialist or doctor will counsel the patient to consider using a hearing aid. If the patient chooses to purchase a hearing aid, the hearing specialist or doctor has to spend additional time to fit the hearing aid for the patient. All these services are expensive and usually not covered by insurance or the government.

As noted above, the conventional hearing loss testing is performed using an audiometer. The audiometer presents a calibrated pure tone signal to the patient via a transducer such as a headphone, an insert earphone, or a loud-speaker to one of the patients two ears. If the patient hears the tone, the level of the tone will be reduced and presented to the patient again. If the patient cannot hear the tone, the level of the tone will be increased and presented to a patient again. This procedure will repeat many times until certain number of reversals from decreasing the tone to increasing the tone has been reached. The hearing threshold of the patient is defined as the signal level at which the patient can hear the tone 50% percent of the time the tone is presented to the patient. The hearing threshold can be derived from the various reversal levels. For each ear, the above procedure is usually repeated at 125, 250, 500, 1000, 2000, 4000, and 8000 Hz. If the difference of the hearing thresholds at two adjacent frequencies exceeds a critical value (e.g., 20 dB), an additional test can be performed at a middle frequency. Often middle frequencies are only applied, when needed, for frequencies between 500 to 8000 Hz. Accordingly, the maximum number of testing frequencies is usually eleven (e.g., 125, 250, 500, 750, 1500, 2000, 3000, 4000, 6000, and 8000 Hz).

In order for the hearing loss test results to be meaningful, the testing system (namely, the audiometer) must be calibrated. In other words, the relationship between the electrical settings in the system and the acoustical pressure delivered to subject must be known. Various components affect the calibration including, but not limited to, electrical system that generates the stimuli and listening system (transducer) that converts electrical signal into acoustic pressure. Calibration is further complicated by the fact that sound level measured at the eardrum of a human varies from person to person even when delivered with the same system and identical settings. As a result, calibration of a testing system is often conventionally done using a special coupler for which a reference hearing level of normal listeners has been established. For example, the audiometer with an insertion earphone is usually calibrated in a 2 cubic-centimeters (cc) coupler. When listeners with normal hearing listen to pure tones through an insertion earphone, the sound levels, as measured in the 2 cc coupler, of the pure tones need to be set to the following levels (given in Sound Pressure Level (SPL)) for the sounds to be just audible:

| Frequency (Hz) | Level (dB SPL) |
|---|---|
| 125 | 45 |
| 250 | 35 |
| 500 | 20 |
| 750 | 15 |
| 1000 | 10 |
| 1500 | 8 |
| 2000 | 7 |
| 3000 | 12 |
| 4000 | 20 |
| 6000 | 27 |
| 8000 | 30 |

The above levels are called normal reference levels of the insertion earphone in the 2 cc coupler. The reference levels vary for different transducers as well as different couplers.

Hearing thresholds for a patient are usually expressed in decibels hearing level (db HL), which is relative level in reference to the normal reference levels. The reference levels should have been established for the system and transducer used in the test. For example, the normal reference level for an insertion earphone is 7 dB SPL at 2000 Hz as measured in a 2 cc coupler. If the hearing level for a patient is 47 dB SPL at the same frequency as measured in the same 2 cc coupler, the hearing loss for the patient is 47−7=40 dB HL. For most commercial audiometers, the normal reference levels can be built-in the machine, and the signal level presented to patient is automatically expressed in dB HL.

Accordingly, there are various problems associated with conventional hearing loss testing. One problem with conventional hearing loss testing is that specialized testing equipment must be used and that the testing equipment must be calibrated. Another problem with conventional hearing loss testing is the costs and often limited availability of hearing specialists or ENT doctors to administrator the hearing loss examination. As a result, for various reasons, hearing loss testing and hearing loss assistance are generally not readily available to people.

Thus, there is a need for improved approaches to evaluating hearing loss and assisting those with hearing loss to obtain hearing assistance products or services.

SUMMARY OF THE INVENTION

Broadly speaking, the invention relates to improved ways to assist those having hearing loss. One aspect of the invention pertains to providing on-line hearing loss testing. The on-line hearing loss testing can be self-performed without any specialized equipment. Another aspect of the invention pertains to on-line sound customization. The sound customization can simulate hearing compensation on-line. As an example, the hearing compensation can be used to simulate hearing aid processing. The sound customization can also simulate hearing loss. Still another aspect of the invention pertains to a recommendation and/or referral procedure. Yet another aspect of the invention pertains to on-line hearing aid purchasing.

The invention can be implemented in numerous ways including as a method, system, apparatus, device, and computer readable medium. Several embodiments of the invention are discussed below.

As a method for determining an amount of hearing loss for a participating subject, one embodiment of the invention includes the acts of: performing a first on-line hearing loss test for a reference subject to produce reference parameters; performing a second on-line hearing loss test for the participating subject to produce participant parameters; and determining relative hearing loss for the participating subject based on the participant parameters and the reference parameters.

As an on-line method for providing hearing aid processing, one embodiment of the invention includes the acts of: performing an on-line diagnosis of a user's hearing loss; determining hearing aid parameters based on the on-line diagnosis; modifying an electronic sound source based on the hearing aid parameters to produce a modified electronic sound source; and playing the modified electronic sound source for the user.

As an on-line method for providing hearing aid processing, one embodiment of the invention includes the acts of: receiving hearing loss data on-line for a user; determining hearing aid parameters based on the hearing loss data; modifying an electronic sound source based on the hearing aid parameters to produce a modified electronic sound source; and playing the modified electronic sound source for the user.

As a method for referring a hearing impaired listener to a hearing product or service specialist, one embodiment of the invention includes the acts of: receiving hearing loss data on-line for a hearing impaired user; receiving a selection of one of a plurality of hearing product or service providers; directing the hearing impaired listener to the selected one of the the hearing product or service providers; and forwarding the hearing loss data for the hearing impaired listener to the selected one of the hearing product or service providers over a data network. Optionally, the hearing loss of the hearing impaired listener can be determined on-line.

As an on-line method for providing impaired hearing simulation, one embodiment of the invention includes the acts of: receiving hearing loss data on-line for a first user, the first user being hearing impaired; modifying an electronic sound source based on the hearing less data to produce an impaired electronic sound source; and playing the impaired electronic sound source for second user, the second user being substantially non-hearing impaired.

As a computer readable medium including computer program code for determining an amount of hearing loss for a participating subject, one embodiment of the invention includes: computer program code for performing a first on-line hearing loss test for a reference subject to produce reference parameters; computer program code for performing a second on-line hearing loss test for the participating subject to produce participant parameters; and computer program code for determining relative hearing loss for the participating subject based on the participant parameters and the reference parameters.

As a computer readable medium including computer program code for providing on-line hearing aid processing, one embodiment of the invention includes: computer program code for accessing an on-line diagnosis of a user's hearing loss; computer program code for determining hearing aid parameters based on the on-line diagnosis; computer program code for modifying an electronic sound source based on the hearing aid parameters to produce a modified electronic sound source; and computer program code for transmitting the modified electronic sound source for the user.

As a computer readable medium including computer program code for referring a hearing impaired listener to a hearing product or service specialist, one embodiment of the invention includes: computer program code for determining hearing loss of the hearing impaired listener on-line, the hearing loss being represented in hearing loss data; computer program code for receiving a selection of one of a plurality of hearing product or service providers; computer program code for directing the hearing impaired listener the selected one of the hearing product or service providers; and computer program code for forwarding the hearing loss data for the hearing impaired listener to the selected one of the hearing product or service providers over a data network.

The advantages of the invention are numerous. Different embodiments or implementations may yield one or more of the following advantages. One advantage of the invention is that hearing tests are able to be performed on-line. Another advantage of the invention is that no expensive specialized equipment or personnel is needed for performing hearing tests. Another advantage of the invention is that near real-time sound customization can be performed. Still another advantage of the invention is that on-line simulation of hearing aid processing can be performed. Yet another advantage of the invention is that once hearing loss is diagnosed, proper hearing aids can be recommended and/or purchased on-line, and/or referrals can be made to suitable service or product providers. Still yet another advantage of the invention is that the data obtained from the hearing tests can be archived for later usage or forwarded to suitable service or product providers.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which:

FIG. 7 is a screen depiction of a user interface for a local machine;

DETAILED DESCRIPTION OF THE INVENTION

The invention relates to improved ways to assist those having hearing loss. One aspect of the invention pertains to providing on-line hearing loss testing. The on-line hearing loss testing can be self-performed without any specialized equipment. Another aspect of the invention pertains to on-line sound customization. The sound customization can simulate hearing compensation on-line. As an example, the hearing compensation can be used to simulate hearing aid processing. Still another aspect of the invention pertains to a recommendation and/or referral procedure.

Embodiments of this aspect of the invention are discussed below with reference to FIGS. 1–9. However, those skilled in the art will readily appreciate that the detailed description given herein with respect to these figures is for explanatory purposes as the invention extends beyond these limited embodiments.

Figure 1:
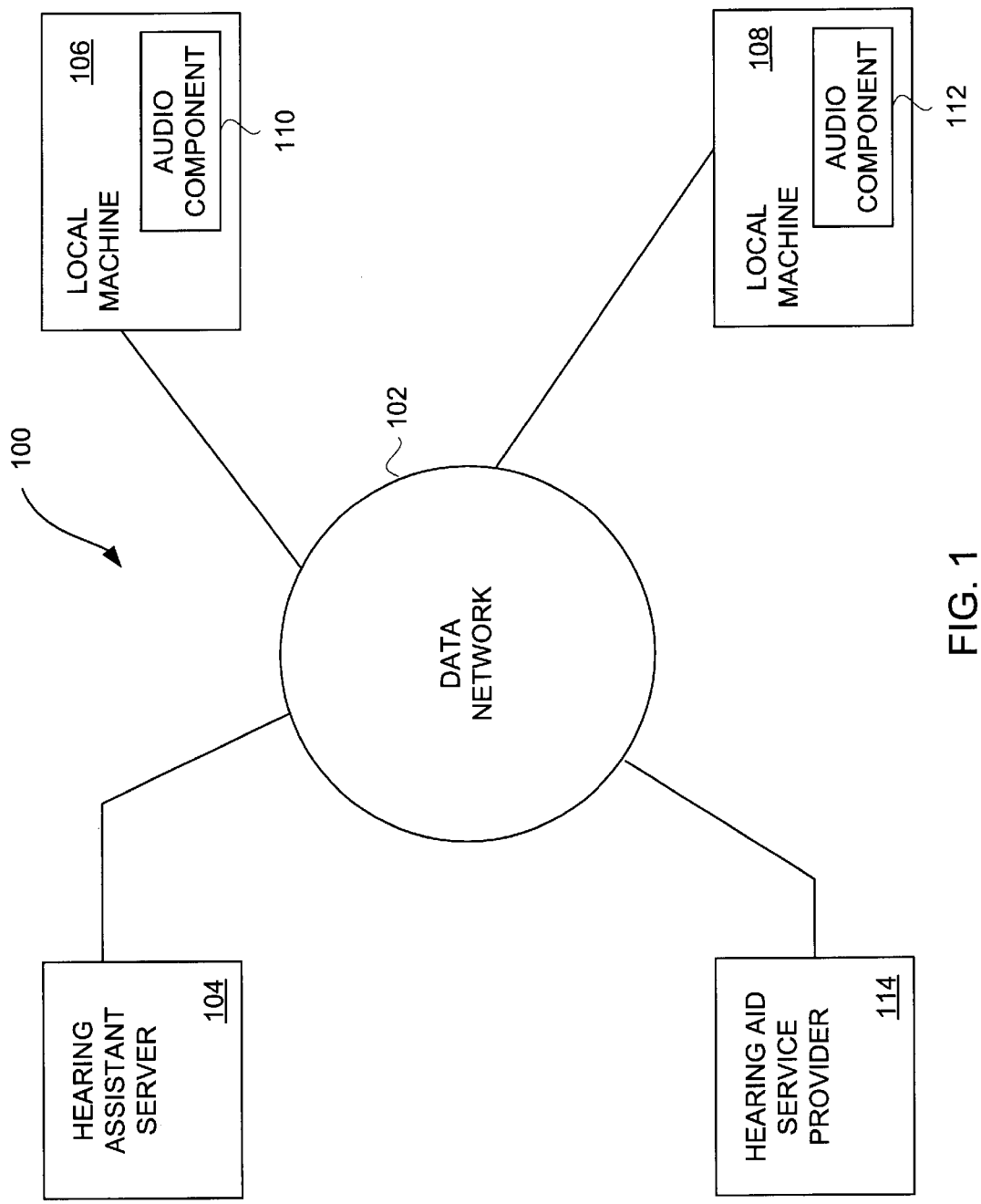
FIG. 1 is a network-based hearing evaluation and compensation system according to one embodiment of the invention.

FIG. 1 is a network-based hearing evaluation and compensation system 100 according to one embodiment of the invention. The network-based hearing evaluation and compensation system 100 includes a data network 102. The data network 102 can take a variety of forms. The data network 102 provides a communication network through which a hearing assistant server 104 can communicate with local machines 106 and 108. For example, the data network 102 can be or include the Internet, a wide area network (WAN), or a local area network (LAN). The data network 102 can also include a telephone network or a cable network. The data network 102 can also be wired or wireless, or a combination of both.

As shown in FIG. 1, the local machine 106 includes an audio component 110 and the local machine 108 includes an audio component 112. It should be understood that the network-based hearing evaluation and compensation system 100 can include one or more local machines, such as the local machines 106 and 108. The audio components 110 and 112 of the local machines 106 and 108, respectively, provide for an audio (or sound) output at the local machine. A sound output provided by the audio components 110 and 112 is directed at a subject. Typically, the subject is the user of the corresponding local machine. The audio components 110 and 112 can take a variety of forms. For example, the audio components 110 and 112 can pertain to a sound card residing in the local machine together with a speaker(s) (loudspeaker(s)), earphone or headset. As another example, the audio components 110 and 112 can pertain to a peripheral device that couples to the local machine. In one implementation, the local machine is a personal computer and thus typically includes one or more audio components. In another implementation, the local machine has a network browser thereon for accessing the data network 102.

The network-based hearing evaluation and compensation system 100 operates in a client-server manner, wherein the hearing assistant server 104 is the server and the local machines 106 and 108 are clients. The local machines 106 and 108 can interact with the hearing assistant server 104 to perform on-line hearing evaluations (examinations). As noted above, the hearing evaluations are for subjects, which are typically the users at the local machines. In addition, the local machines 106 and 108 can also access the hearing assistant server 104 to simulate hearing corrections for the subjects (users). For example, if a user of a particular local machine desires to hear a music file residing on the hearing assistant server 104 (or other remote server device coupled the data network 102), the hearing assistant server 104 can manipulate the standard sound file to provide for corrections that are associated with compensating for the hearing loss associated with the user of the particular local machine. Consequently, the user of the local machine can hear the sound after it has been corrected for their particular hearing loss.

Furthermore, the network-based hearing evaluation and compensation system 100 can also include a hearing aid service provider 114. Typically, the local machines 106 and 108 can access the hearing aid service provider 114 through the data network 102. In addition, the hearing assistant server 104 can refer or direct certain subjects (users) to the hearing aid service provider 114. Typically, the referral could be made after the subject has indicated a desire for a hearing aid product or service that is offered by the hearing aid service provider 114. The on-line results of the hearing evaluation for the subject can also be forwarded to the hearing aid service provider 114 with the referral. Although only a single hearing aid service provider is illustrated in FIG. 1, it should be understood that the network-based hearing evaluation and compensation system 100 would typically service a plurality of hearing aid service providers.

Figure 2:
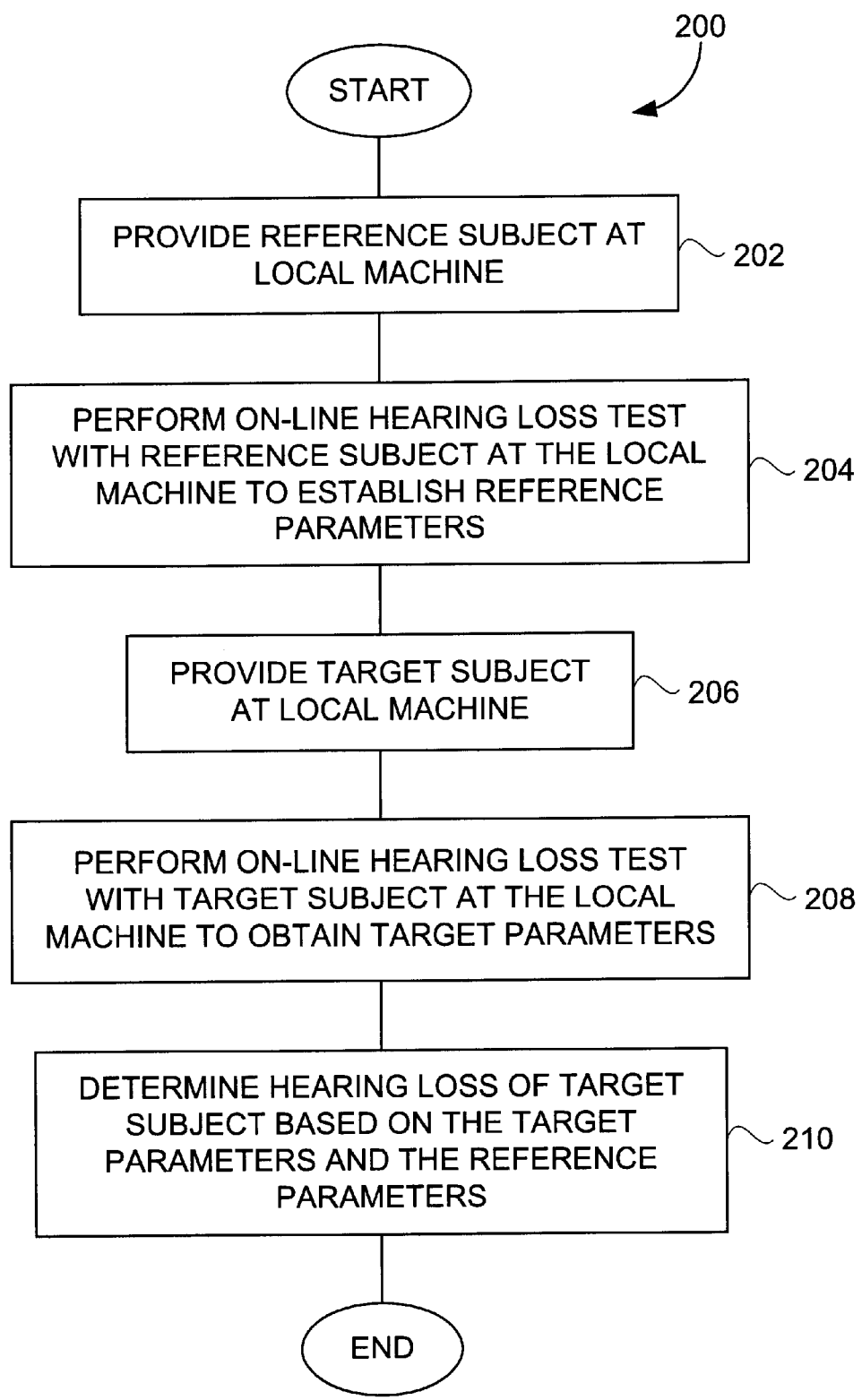
FIG. 2 is a block diagram of relative hearing loss evaluation processing according to one embodiment of the invention.

FIG. 2 is a block diagram of relative hearing loss evaluation processing 200 according to one embodiment of the invention. The relative hearing loss evaluation processing 200 initially provides 202 a reference subject at a local machine. As examples, the reference subject can be a young person known to have normal hearing, a person whose hearing loss is known, or a person whose hearing can be identified as normal hearing such as by listening to some natural sounds or sounds generated from special devices that have been calibrated to produce sound at certain levels. The local machine is, for example, a personal computer having a network browser thereon. Next, an on-line hearing loss test is performed 204 with the reference subject at the local machine. The on-line hearing test establishes reference parameters. In one embodiment, these reference parameters are normal reference levels. The particulars of hearing loss tests, such as tone frequency and amplitude, are generally well known in the art. However, according to the invention, the hearing loss test is performed on-line. As an example, the on-line hearing loss test can be controlled by the hearing assistant server 104 illustrated in FIG. 1 such that the reference subject positioned proximate to the local machine 106 or 108 can receive sound signals associated with the hearing loss test and respond them at the local machine. At this point having performed the on-lined hearing loss test with respect to the referenced subject, reference parameters for various frequencies are known.

Next, by using these reference perimeters as a base line condition, the relative hearing loss of a particular subject (target subject) can be determined. Once there is a target subject that desires his or her hearing to be evaluated, the relatively hearing loss evaluation processing 200 continues. Namely, the target subject is provided 206 at the local machine. The local machine used by the target subject is the same local machine that was used by the reference subject to obtain the referenced perimeters at operation 204. After the target subject is provided 206 at the local machine, an on-line hearing loss test is performed 208 with the target subject at the local machine. The on-line hearing loss test establishes target parameters. In one embodiment, the target parameters are hearing loss levels.

Thereafter, hearing loss of the target subject can be determined 210 based on the target perimeters and the referenced perimeters. In one embodiment, the hearing loss is expressed as various hearing thresholds for different frequencies. Typically, the hearing loss is expressed relative to normal hearing as determined by the reference parameters (such as numerical values relative to the reference parameters). After the hearing loss has been determined 210, the relative hearing loss evaluation processing 200 ends. Note that relative hearing loss evaluation processing 200 does not require any special purpose hardware, merely a local machine (e.g., personal computer having a network browser with access to a data network) and an audio component (e.g., sound card and speaker).

Although in FIG. 2 the reference subject is tested before the target subject, the reverse situation can be also used. Namely, the target subject can be tested first and then subsequently the reference subject tested. Further, the test data from the testing of a single reference subject can be used to test one or many different target subjects. In any case, settings at the local machine that affect its audio output should not be altered or modified between testing of the reference and the target(s) subjects.

Figure 3:
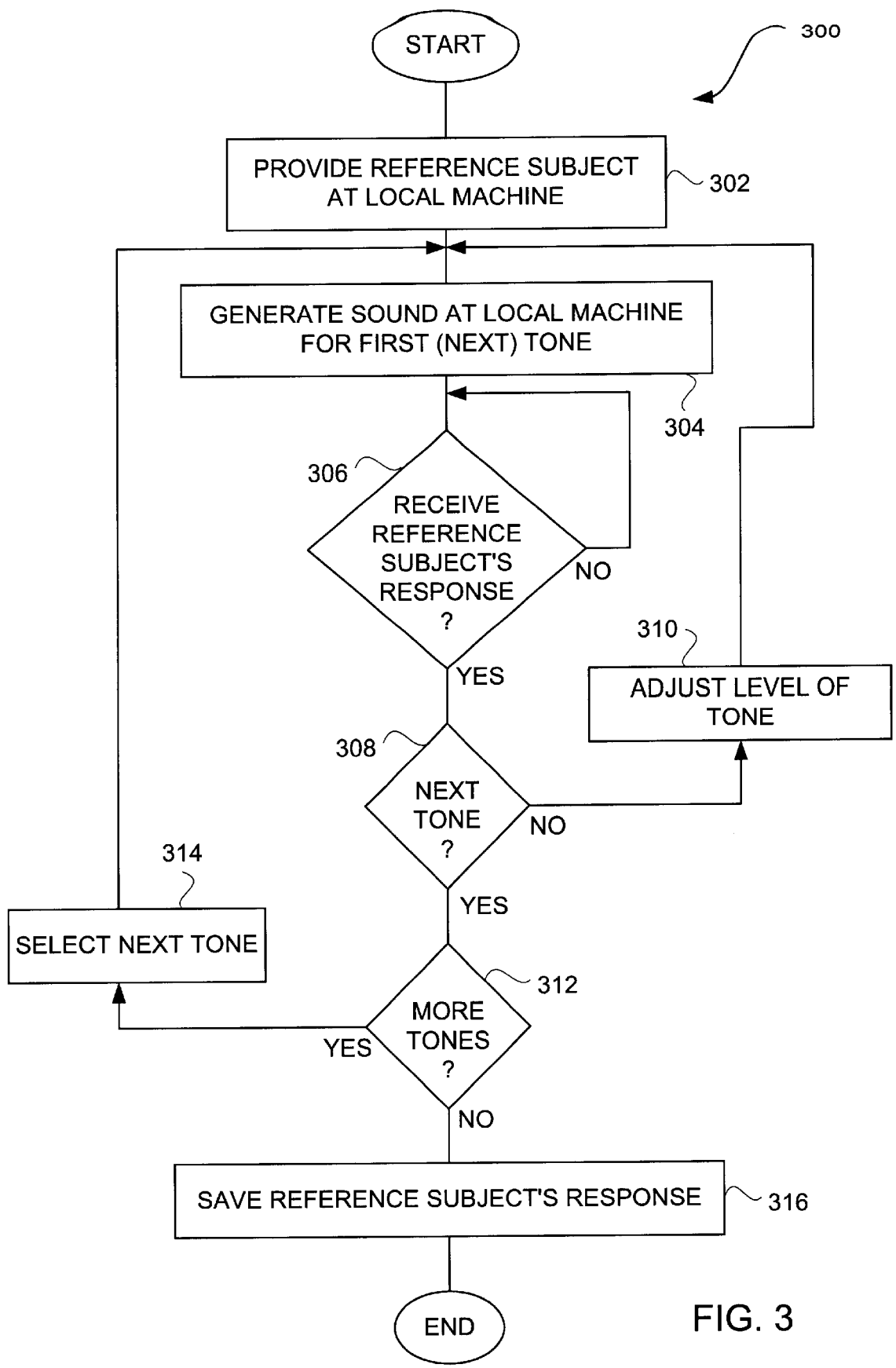
FIG. 3 is a flow diagram of reference subject hearing loss processing according to one embodiment of the invention.

FIG. 3 is a flow diagram of reference subject hearing loss processing 300 according to one embodiment of the invention. The reference subject hearing loss processing 300 is, for example, additional detail on the operations performed with respect to the on-line hearing loss test for the reference subject at operation 204 illustrated in FIG. 2.

The reference subject hearing loss processing 300 initially provides 302 a reference subject at a local machine. Then, sound is generated 304 at the local machine for a first tone. A decision 306 then determines whether the reference subject's response to the sound generated 304 at the local machine has been received. When a decision 306 determines that the reference subject's response is not yet received, the reference subject hearing loss processing 300 awaits such a response. Once the decision 306 determines that the reference subject's response has been received, a decision 308 determines whether a next tone should be processed. When a decision 308 determines that the next tone should not yet be processed, then the level of the tone (current tone) is adjusted 310. Here, the level of the tone is typically adjusted up or down and then the processing returns to repeat the operation 304 and subsequent operations. On the other hand, when the decision 308 determines that a next tone is to be processed, then a decision 312 determines whether there are additional tones to be processed. When a decision 312 determines that there are additional tones to be processed, the next tone is selected 314. Following the selection 314 of the next tone, the reference subject hearing loss processing 300 returns to repeat the operation 304 and subsequent operations. Alternatively, when a decision 312 determines that there are no more tones to be processed, the reference subject's response is saved 316. After saving 316 the reference subject's response, the reference subject hearing loss processing 300 is complete and ends.

Figure 4:
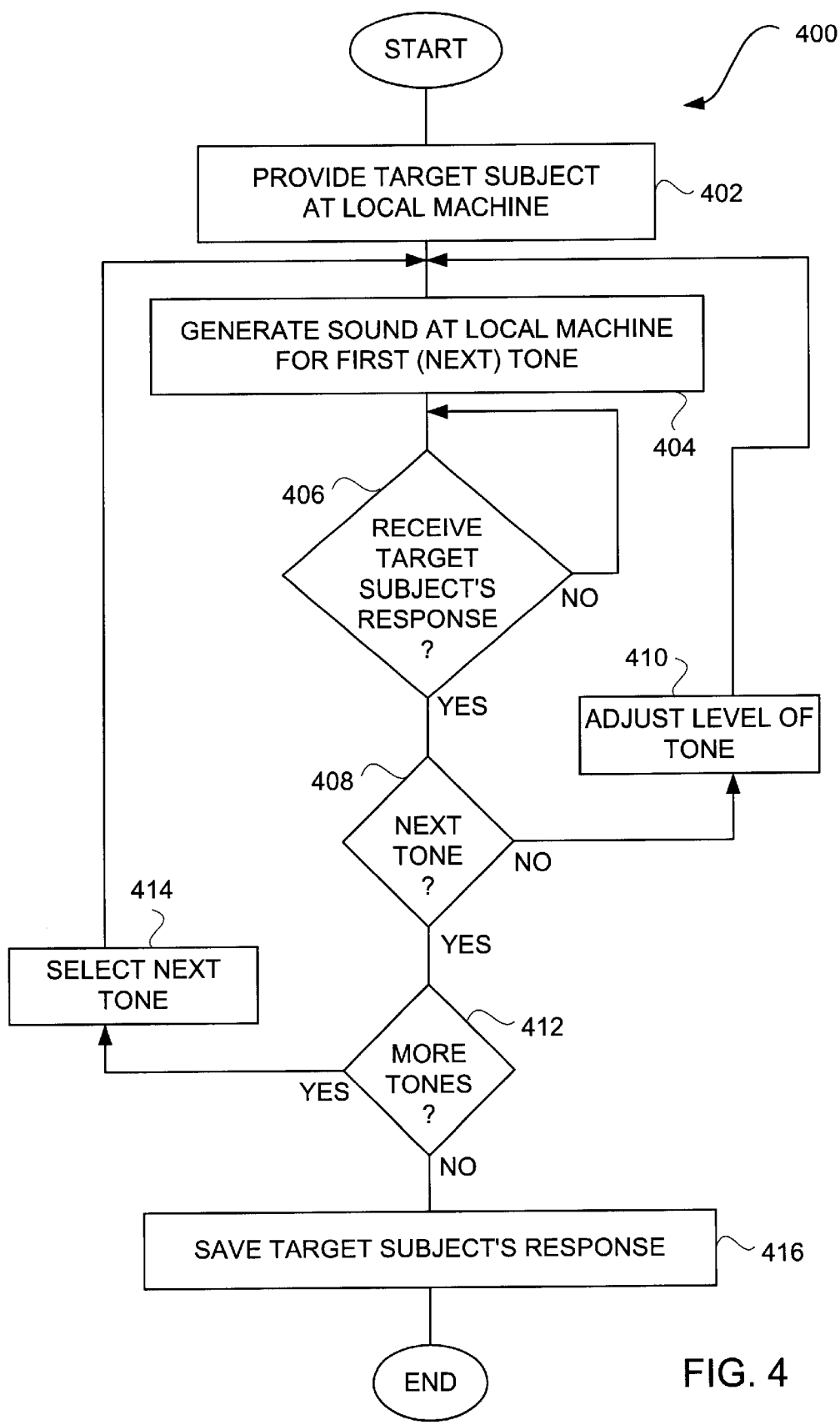
FIG. 4 is a flow diagram of target subject hearing loss processing according to one embodiment of the invention.

FIG. 4 is a flow diagram of target subject hearing loss processing 400 according to one embodiment of the invention. The target subject hearing loss processing 400 is generally similar to the reference subject hearing loss processing 300 illustrated in FIG. 3. One notable difference is that the target subject hearing loss processing 400 pertains to a particular target subject, whereas the reference subject hearing loss processing 300 pertains to a reference subject. The target subject hearing loss processing 400 is, for example, additional detail on the operations performed with respect to the on-line hearing loss test for the target subject at operation 208 illustrated in FIG. 2.

The target subject hearing loss processing 400 initially provides 402 a target subject at a local machine. Then, sound is generated 404 at the local machine for a first tone. A decision 406 then determines whether the target subject's response to the sound generated 404 at the local machine has been received. When a decision 406 determines that the target subject's response is not yet received, the target subject hearing loss processing 400 awaits such a response. Once the decision 406 determines that the target subject's response has been received, a decision 408 determines whether a next tone should be processed. When a decision 408 determines that the next tone should not yet be processed, then the level of the tone (current tone) is adjusted 410. Here, the level of the tone is typically adjusted up or down and then the processing returns to repeat the operation 404 and subsequent operations. On the other hand, when the decision 408 determines that a next tone is to be processed, then a decision 412 determines whether there are additional tones to be processed. When a decision 412 determines that there are additional tones to be processed, the next tone is selected 414. Following the selection 414 of the next tone, the target subject hearing loss processing 400 returns to repeat the operation 404 and subsequent operations. Alternatively, when a decision 412 determines that there are no more tones to be processed, the target subject's response is saved 416. After saving 416 the target subject's response, the target subject hearing loss processing 400 is complete and ends.

Further, with respect to the hearing loss processing 300 and 400, the sounds or tones presented to the subject are, for example, preferably pure tones. The local machine generates the sounds (such as with a sound card) and outputs the sounds to the subject through a speaker, an earphone, or a headset. It should be noted that the sounds can be specifically generated on-demand from the sound card or produced using predetermined sound files. The subject's response (i.e., whether they hear the sound or not) can be input to the local machine through a wide range of input devices. One input method is through use of a mouse and a graphical user interface (see FIG. 7). Typically, for each tone a reversal sequence is followed. When the subject responds (indicates) that they hear the tone, the level of the tone will be reduced and presented to the subject again. When the subject responds (indicates) that they cannot hear the tone, the level (i.e., amplitude) of the tone will be increased and presented to the subject again. This procedure will repeat many times until a certain number of reversals from decreasing the tone to increasing the tone has been reached, thereby completing the reversal sequence. The levels for the tones can be generated by particular control of the sound card or by selection of the predetermined sound file for a given tone and amplitude. The hearing threshold of the subject is defined as the signal level at which the patient can hear the tone 50% percent of the time the tone is presented to the patient. The hearing threshold can be derived from the various reversal levels. For each ear, the above procedure is usually repeated at 125, 250, 500, 1000, 2000, 4000, and 8000 Hz. Further, if the difference of the hearing thresholds at two adjacent frequencies exceeds a critical value (e.g., 20 dB), an additional test can be performed at a middle frequency. Often middle frequencies are only applied, when needed, for frequencies between 500 to 8000 Hz. Accordingly, the maximum number of testing frequencies is usually eleven (e.g., 125, 250, 500, 750, 1500, 2000, 3000, 4000, 6000, and 8000 Hz). From the various responses provided, the hearing related parameters are determined. Typically, these hearing related parameters are threshold levels for the subject's hearing at the various frequencies tested.

Instead of the reference subject hearing loss processing 300, the reference subject hearing loss can also be used to adjust audio levels at the location machine. Here, a continuous sound (e.g., pulsed or continuous pure tone) is presented to the reference subject. Then, the reference subject adjusts the audio sound output such that it is just audible. Such volume adjustment can be achieved in a variety of ways, such as speaker volume control, volume control displayed on a graphical user interface, or software control. Hence, this approach is another way to set the reference hearing level, though it is less precise than the reference subject hearing loss processing 300.

Figure 5A:
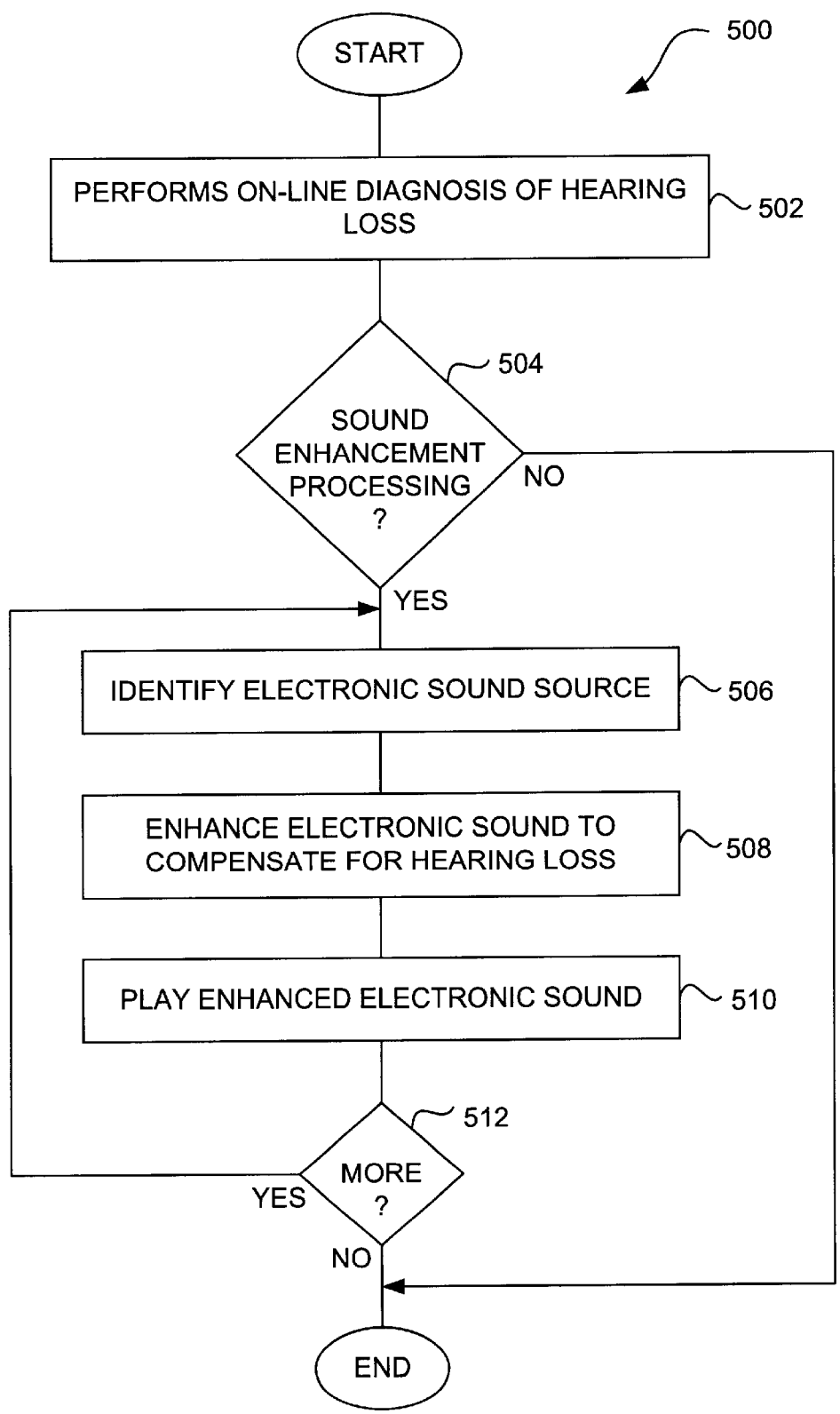
FIG. 5A is a flow diagram of on-line sound processing according to one embodiment of the invention.

FIG. 5A is a flow diagram of on-line sound processing 500 according to one embodiment of the invention. The on-line sound processing 500 provides customized sound for users over a data network. The sound is customized to the particular users in accordance to determined hearing losses of such users. In other words, for a particular user, the on-line sound processing 500 operates to render generic sound into customized sound that compensates (i.e., make certain corrections for) the hearing loss of the user.

The on-line sound processing 500 initially performs 502 an on-line diagnosis of hearing loss. The on-line diagnosis of hearing loss is associated with a particular user. For example, the on-line diagnosis of hearing loss can be determined using the processing as shown in FIG. 2.

After the on-line diagnosis has been performed 502 (or alternatively the diagnosis is retrieved from a previous determination), a decision 504 determines whether sound enhancement processing is desired (or requested). When a decision 504 determines that sound enhancement processing is not desired, then the on-line sound processing 500 is complete and ends without any sound enhancement being performed. In this case, the on-line sound processing is effectively not performed.

On the other hand, when the decision 504 determines that sound enhancement processing is desired (or requested), then an electronic sound source is identified 506. Here, the electronic sound source could be a predetermined sound source, could be selected by a user operation, or could be automatically selected by a server (e.g., the hearing assistance server 104 illustrated in FIG. 1). Examples of electronic sound sources include audio files such as way files, MP3 files, etc. Next, the electronic sound associated with the identified electronic sound source is enhanced 508 to compensate for the hearing loss of the user. Here, the electronic sound is customized to compensate for the hearing loss of the user. Typically, the sound customization would be performed at a remote server (e.g., hearing assistant server 104), but could also be performed locally on the local machine of the user. Next, the enhanced electronic sound is played 510. When being played at a local machine, the user of the local machine whose hearing loss has been diagnosed on-line, is then able to better hear the electronic sound associated with the electronic sound source. The enhanced electronic sound can be made available in near real-time or can instead result in a customized audio file that can be saved and played as desired. Thereafter, a decision 512 determines whether there is more electronic sound to be processed. When the decision 512 determines that there is more electronic sound to be processed, the on-line sound processing 500 returns to repeat the operation 506 and subsequent operations so that additional electronic sounds can be processed in a similar manner. Once the decision 512 determines that there is no more electronic sound to be processed, the on-line sound processing 500 is complete and ends.

Figure 5B:
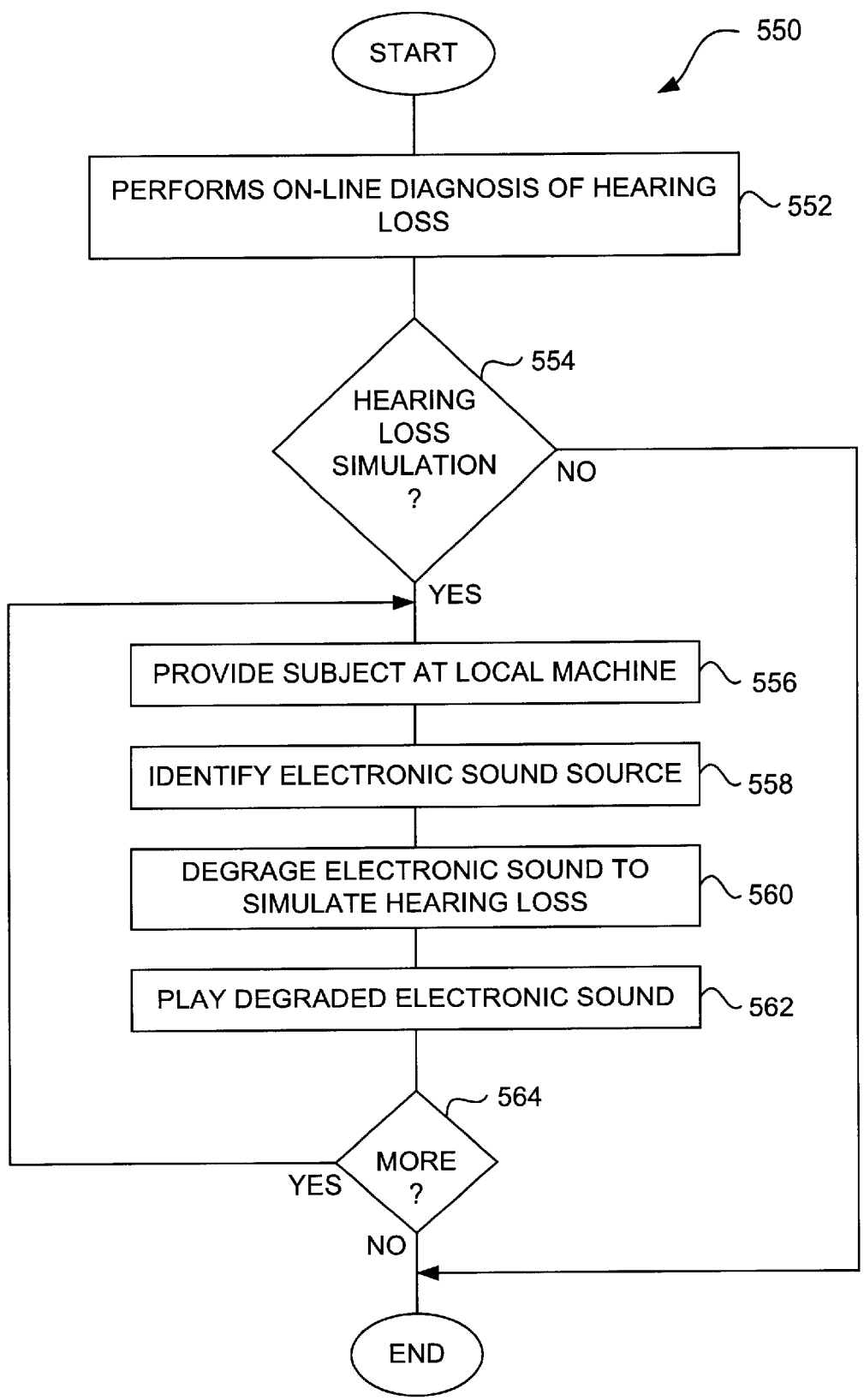
FIG. 5B is a flow diagram of on-line hearing loss simulation processing 550 according to one embodiment of the invention.

FIG. 5B is a flow diagram of on-line hearing loss simulation processing 550 according to one embodiment of the invention. The on-line hearing loss simulation processing 550 provides a subject the ability to hear sound that has been distorted to simulate a hearing loss. This allows persons with normal hearing to hear how sounds will be heard by someone that is hearing impaired.

The on-line hearing loss simulation processing 550 initially performs 552 an on-line diagnosis of hearing loss. The on-line diagnosis of hearing loss is associated with a particular user (subject) with hearing loss. For example, the on-line diagnosis of hearing loss can be determined using the processing as shown in FIG. 2. After the on-line diagnosis has been performed 552 (or alternatively the diagnosis is retrieved from a previous determination), a decision 554 determines whether hearing loss simulation processing is desired (or requested). When the decision 554 determines that hearing loss simulation is not desired, then the on-line hearing loss simulation processing 550 is complete and ends without any hearing loss simulation being performed. In this case, the on-line hearing loss simulation is effectively not performed.

On the other hand, when a decision 554 determines that hearing loss simulation processing is desired (or requested), then a normal subject is provided 556 at the local machine if not already at the local machine. Often, the normal subject has a desire to hear how the impaired subject would hear sounds. An electronic sound source is identified 558. Here, the electronic sound source could be a predetermined sound source, could be selected by a user operation, or could be automatically selected by a server (e.g., the hearing assistance server 104 illustrated in FIG. 1). Examples of electronic sound sources include audio files such as .wav files, MP3 files, etc. Next, the electronic sound associated with the identified electronic sound source is degraded 560 to simulate hearing loss according to the hearing loss identified at operation 552. Here, the electronic sound is intentionally degraded to allow the subject to experience an impaired condition. Typically, the sound customization would be performed at a remote server (e.g., hearing assistant server 104), but could also be performed locally on the local machine of the user. Next, the degraded electronic sound is played 562. The degraded electronic sound can be made available in near real-time or can instead result in a customized audio file that can be saved and played as desired. Thereafter, a decision 564 determines whether there is more electronic sound to be processed. When the decision 564 determines that there is more electronic sound to be processed, the on-line sound processing 550 returns to repeat the operation 556 and subsequent operations so that additional electronic sounds can be processed in a similar manner. Once the decision 564 determines that there is no more electronic sound to be processed, the on-line hearing loss simulation processing 550 is complete and ends.

FIGS. 6A–6D are flow diagrams of hearing assistance processing 600 according to one embodiment of the invention. The hearing assistance processing 600 is, for example, processing performed by the hearing assistant server 104 illustrated in FIG. 1. The hearing assistance processing 600 can perform various tasks, such as hearing evaluations, hearing loss reports, referrals, and hearing enhancement simulations, and can perform these tasks in various orders.

The hearing assistance processing 600 initially performs 602 an on-line diagnosis of hearing loss. Next, a decision 604 determines whether a hearing report is desired. When the decision 604 determines that a hearing report is desired, the hearing report can be generated and transmitted 606 to the target subject. As an example, the hearing report can indicate where and to what extent the target subject's hearing is impaired. Alternatively, when the decision 604 determines that a hearing report is not desired, the operation 606 is bypassed.

Next, a decision 608 determines whether the target subject's hearing is impaired. When the decision 608 determines that the target subject's hearing is not impaired (i.e., normal hearing), then the target subject is advised 610 that a hearing aid is not recommended. Thereafter, the hearing assistance processing 600 is complete and ends.

On the other hand, when the decision 608 determines that the target subject's hearing is impaired, then the target subject is advised 612 that a hearing aid is recommended. As this point, the hearing assistance processing 600 can provide additional assistance to the target subject to assist the target subject in obtaining a hearing aid or other hearing assistance product or service. As will be discussed below, the additional assistance can inform the target subject of available hearing aid types, permit on-line simulation of sounds, enable the target subject to be referred to a hearing aid product or service provider, allow on-line purchase of a hearing aid, schedule an appointment with a hearing aid product or service provider, or store hearing loss information for subsequent use.

According to one embodiment, the hearing assistance processing 600 presents 614 the target subject with available hearing aid types. A decision 616 then determines whether the target subject has selected one of the available hearing aid types. When a decision 616 determines that the target subject has made a selection, then the hearing assistance processing 600 determines 618 hearing aid parameters for the target subject. In one implementation, the hearing aid parameters can be specific to the selected hearing aid types. In another implementation, the hearing aid perimeters can be generic to various hearing aid types.

Next, a decision 620 determines whether the target subject desires to perform an on-line simulation. When the decision 620 determines that the target subject does desire on-line simulation, then on-line simulation of sounds with hearing aid processing is performed 622. Here, the on-line simulation enhances the sound for the target subject based on one or both of the selected hearing aid type and the target subject's hearing loss. A decision 624 then determines whether the hearing aid parameters are to be adjusted. The decision 624 can be initiated either automatically or by the target subject's request. In either case, when the decision 624 determines that the hearing aid parameters are to be adjusted, the parameters for hearing aid processing are adjusted 626. Here, the adjustments can be controlled by the target subject or automatically by a server (e.g., the hearing assistant server 104). Thereafter, the hearing assistance processing 600 returns to repeat the operation 622 and subsequent block so that the on-line simulation can continue with the adjusted parameters.

Alternatively, when the decision 624 determines that the hearing aid parameters are not to be adjusted, then a decision 628 determines whether the target subject desires to select another hearing aid type. By providing the target subject the ability to select various different hearing aid types and simulate their operation, the target subject is able to evaluate the different hearing aid types and have some basis to make a selection among them. When a decision 628 determines that the target subject does select another hearing aid type, then the hearing assistance processing 600 returns to repeat the operation 614 and subsequent blocks so that the user is able to select another available hearing aid type and perform an on-line simulation. On the other hand, when a decision 628 determines that the target subject does not desire to selected another hearing aid type, then the hearing assistance processing 600 can select or recommend 630 one or more suitable hearing aids for the target subject. The selection or recommendation can be influenced by feedback received from the target subject. As an example, feedback can be obtained through a questionnaire presented and completed by the target subject. Following operation 630, the on-line simulation is completed. Also, when the decision 620 determines that the target subject does not desire on-line simulation, the operations 622–630 are bypassed.

Further, the hearing assistance processing 600 can determine whether an on-line purchase of a hearing aid is desired. A decision 631 determines whether the target subject desires to purchase a hearing aid on-line. When the decision 631 determines that an on-line purchase is not desired, then the hearing assistance processing 600 can operate to determine whether a referral is desired. Here, a decision 632 determines whether the target subject desires to receive a referral to a suitable hearing aid product or service provider. When the decision 632 determines that a referral is desired, then the target subject is presented 634 with a list of suitable hearing aid product or service providers. Then, a decision 636 determines whether the target subject has selected one of the hearing aid product or service providers. Once the decision 636 determines that the target subject has selected one of the hearing aid product or service providers, then a decision 638 determines whether the target subject desires to make an appointment with the selected product or service provider. When the decision 638 determines that an appointment is to be made, the appointment is scheduled 640. The appointment can be scheduled on-line such as over the Internet or through use of electronic mail. Following the scheduling 640 of the appointment, as well as directly following the decision 638 when an appointment is not to be made, the referral processing is completed. Also, when the decision 632 determines that the referral is not desired, the operations 634–640 are bypassed.

Still further, the hearing assistance processing 600 can operate to cause the hearing loss information of the target subject to be saved 642. The hearing loss information can be saved in a variety of locations depending upon the type of hearing loss information and how it might be used. For example, the hearing loss information could be stored on the hearing assistant server 104 illustrated in FIG. 1 or some other remote server device or associated database that can be accessed via the data network 102. By saving the hearing loss information, comparative studies can be performed, or users can compare a subsequent hearing loss diagnosis with prior ones. Also, by saving the hearing loss information, the hearing loss information can be accessed as need to perform on-line simulations or to produce hearing aids or other hearing correction products or services.

Next, a decision 644 determines whether a hearing loss information should be forwarded. Typically, the hearing loss information would be forwarded to the selected product or service provider so that the product or service provider can thereafter utilize the hearing loss information that has been obtained and perhaps modifications thereto made using on-line simulations. In any case, when the decision 644 determines that the hearing loss information should be forwarded, then the hearing loss information is transmitted 646 to the selected hearing aid service provider. After the hearing loss information has been transmitted 646, as well as directly following the decision 644 when the hearing loss information is not be forwarded, the hearing assistance processing 600 is complete and ends.

Figure 6A:
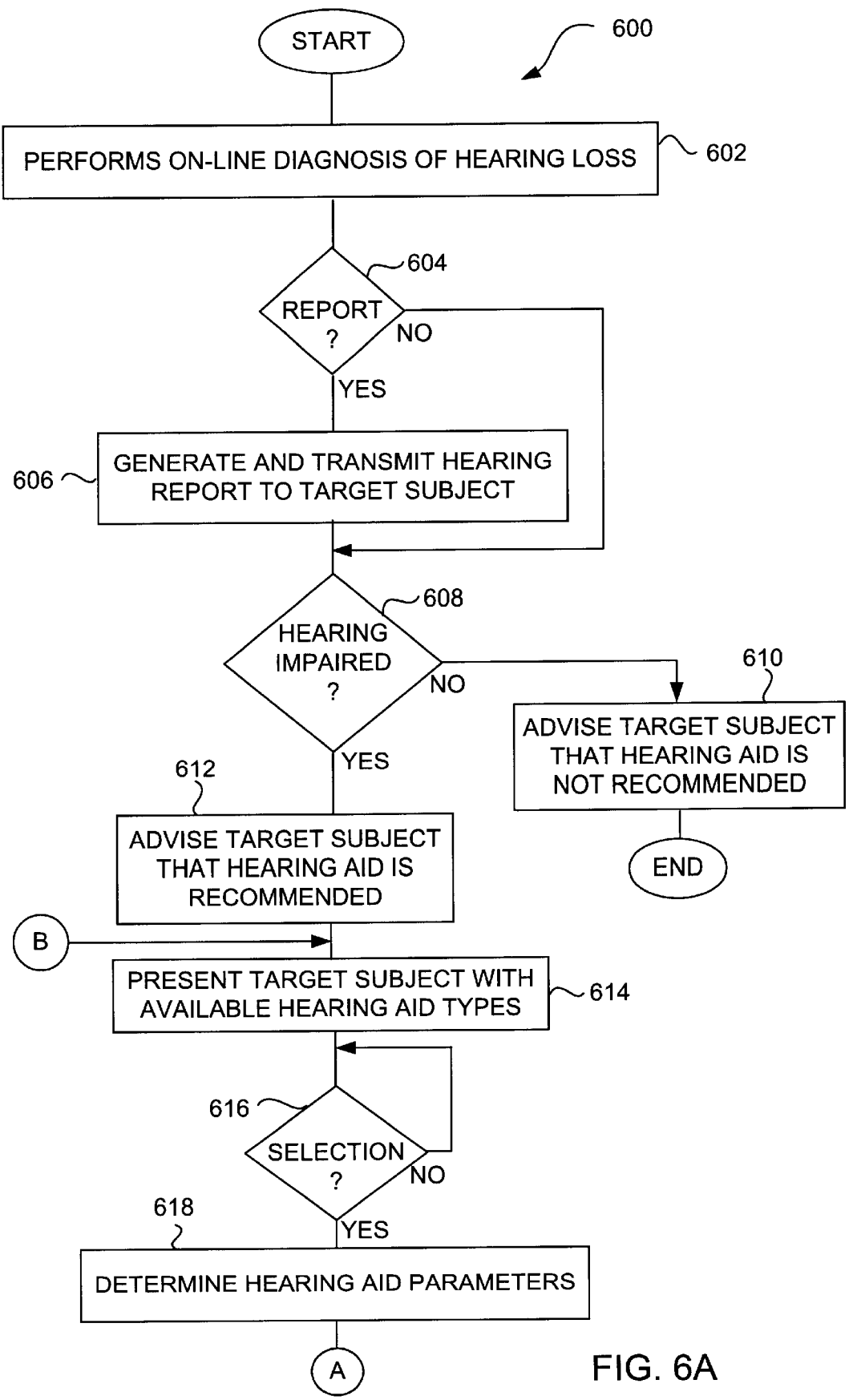
FIGS. 6A–6D are flow diagrams of hearing assistance processing according to one embodiment of the invention.
Figure 6B:
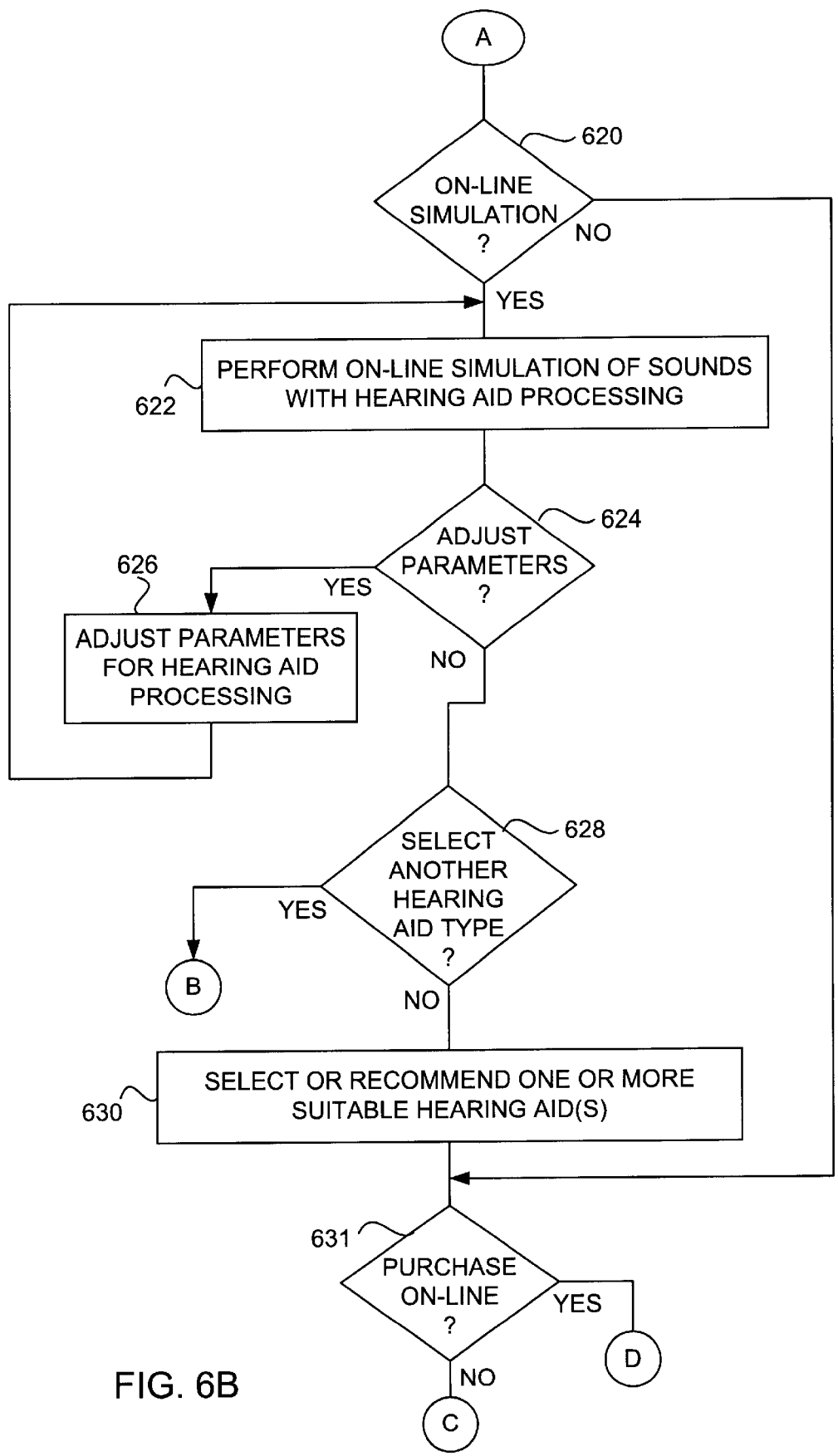
Figure 6C:
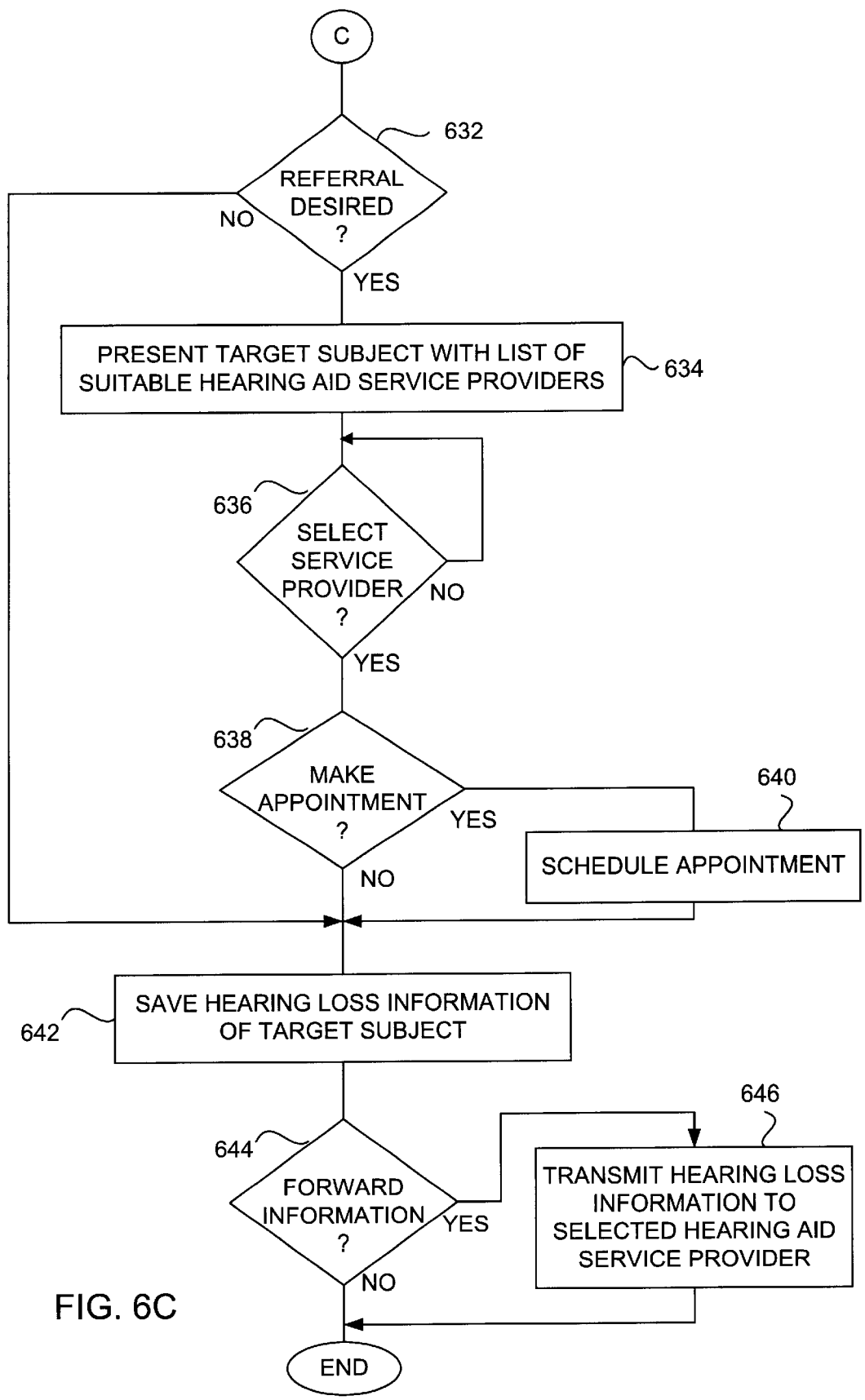
Figure 6D:
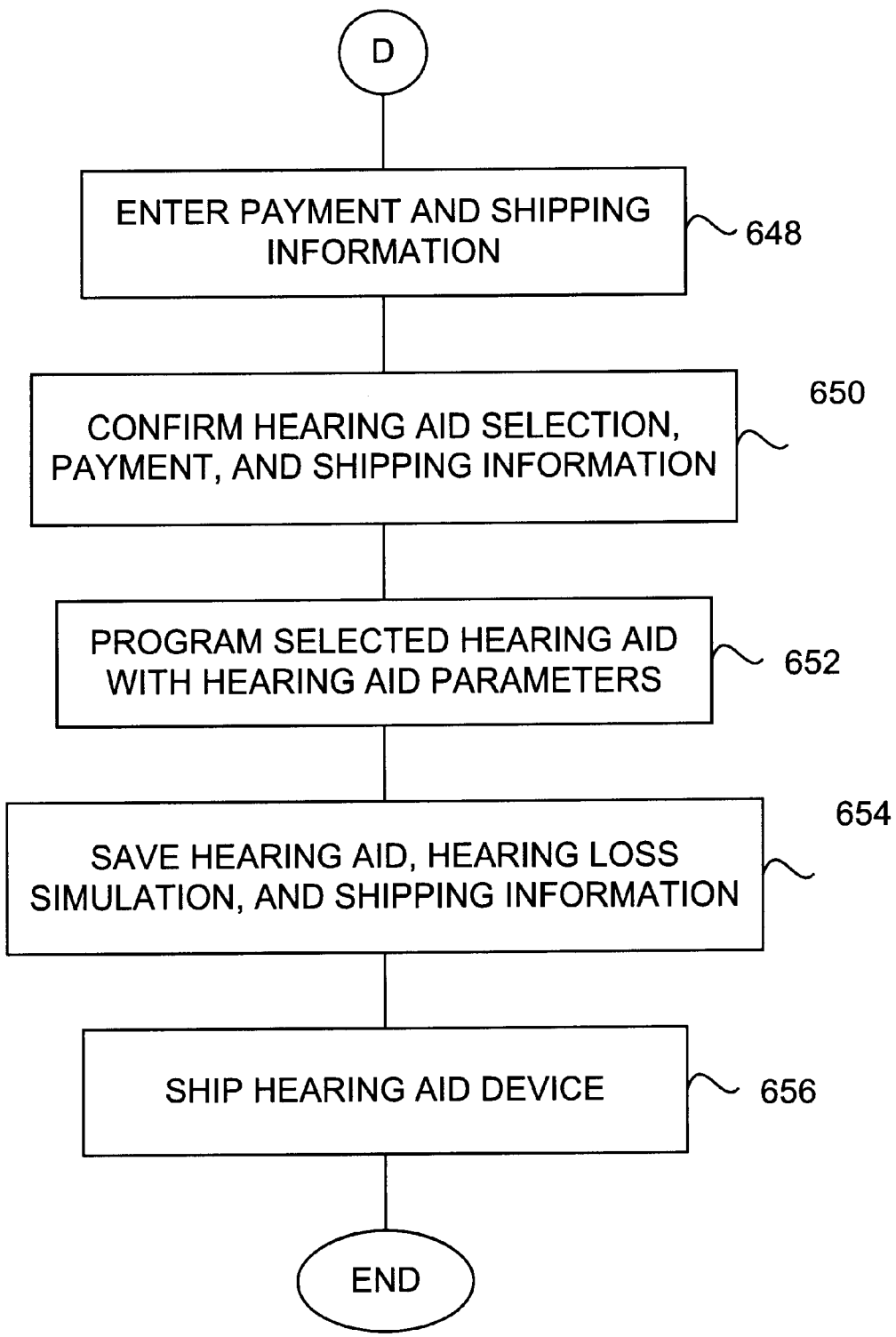

Still further, when the decision 631 determines that the target subject does desire to purchase a hearing aid on-line, the hearing assistance processing 600 performing the operation shown in FIG. 6D to effectuate an on-line purchase. Namely, since a hearing aid has presumably already be selected, payment and shipping information are entered 648. The target subject can, for example, enter this information at the local machine. Then, the hearing aid selection, payment, and shipping information are confirmed 650. To the extent that such information is not already known, it can be entered by the target subject. Next, a hearing-aid provider physically programs 652 a hearing aid device (of the selected hearing aid type) in accordance with the hearing aid parameters previously determined. The target subject may or may not have caused adjustment of the hearing aid parameters, such as through on-line simulation. For future reference, the hearing aid, hearing loss, simulation and shipping information can be saved 654. After the programming 652 of the hearing aid device, the hearing aid device is shipped 656 to the target subject (or other person making the purchase).

In one embodiment, the hearing assistance processing 600 is performed by a server, such as the hearing assistant server 104 illustrated in FIG. 1. However, the hearing assistance processing 600 is also influenced by user input. For example, the subject can indicate whether a hearing report is desired or whether on-line simulation is desired. As other examples, the subject can also influence the hearing assistance processing 600 by selection of hearing aid types or service providers. In another embodiment, portions of the hearing assistance processing 600 can by performed on the local machine.

To further illustrate the hearing assistance processing 600, consider the following example. Here, assume that the on-line diagnosis of hearing loss that is performed (602) yields the following hearing thresholds for a subject.

| Frequency (Hz) | Threshold (dB HL) |
| --- | --- |
| 250 | 20 |
| 500 | 30 |
| 1000 | 40 |
| 2000 | 50 |
| 4000 | 60 |
| 8000 | 70 |

Given that the subject suffers from impaired hearing, the subject selects (616) a hearing aid type. The hearing aid parameters for the selected hearing aid type are then determined (618). Typically, the determination of the hearing aid parameters is dependent on the type of hearing parameter and often on the particular manufacturer. For this example, assume that the following hearing aid parameters are determined for the selected hearing aid type.

| Freq. | Soft-sound-gain | Loud-sound-gain |
| --- | --- | --- |
| 250 | 5 | 1 |
| 500 | 10 | 5 |
| 1000 | 20 | 10 |
| 2000 | 25 | 13 |
| 4000 | 30 | 15 |
| 8000 | 30 | 15 |

Here the hearing aid parameters include various soft-sound gains and loud- sound gains for various frequencies. The soft-sound gains are used for softer incoming sounds, while the loud-sound gains are for louder incoming sounds.

Assume then that on-line simulation is performed (622) and that the hearing aid parameters are adjusted (626). As a result, the hearing aid parameters after adjustment are then as follows.

| Freq. | Soft-sound-gain | Loud-sound-gain |
| --- | --- | --- |
| 250 | 8 | 2 |
| 500 | 13 | 7 |
| 1000 | 22 | 12 |
| 2000 | 27 | 15 |
| 4000 | 34 | 18 |
| 8000 | 34 | 18 |

Note, that adjustments to the hearing aid parameters as compared to those listed above. Hence, the subject or server are able to adjust the hearing aid parameters, or more generally the on-line simulation, to experiment with different adjustments and perhaps improve their listening quality or experience.

Figure 7:
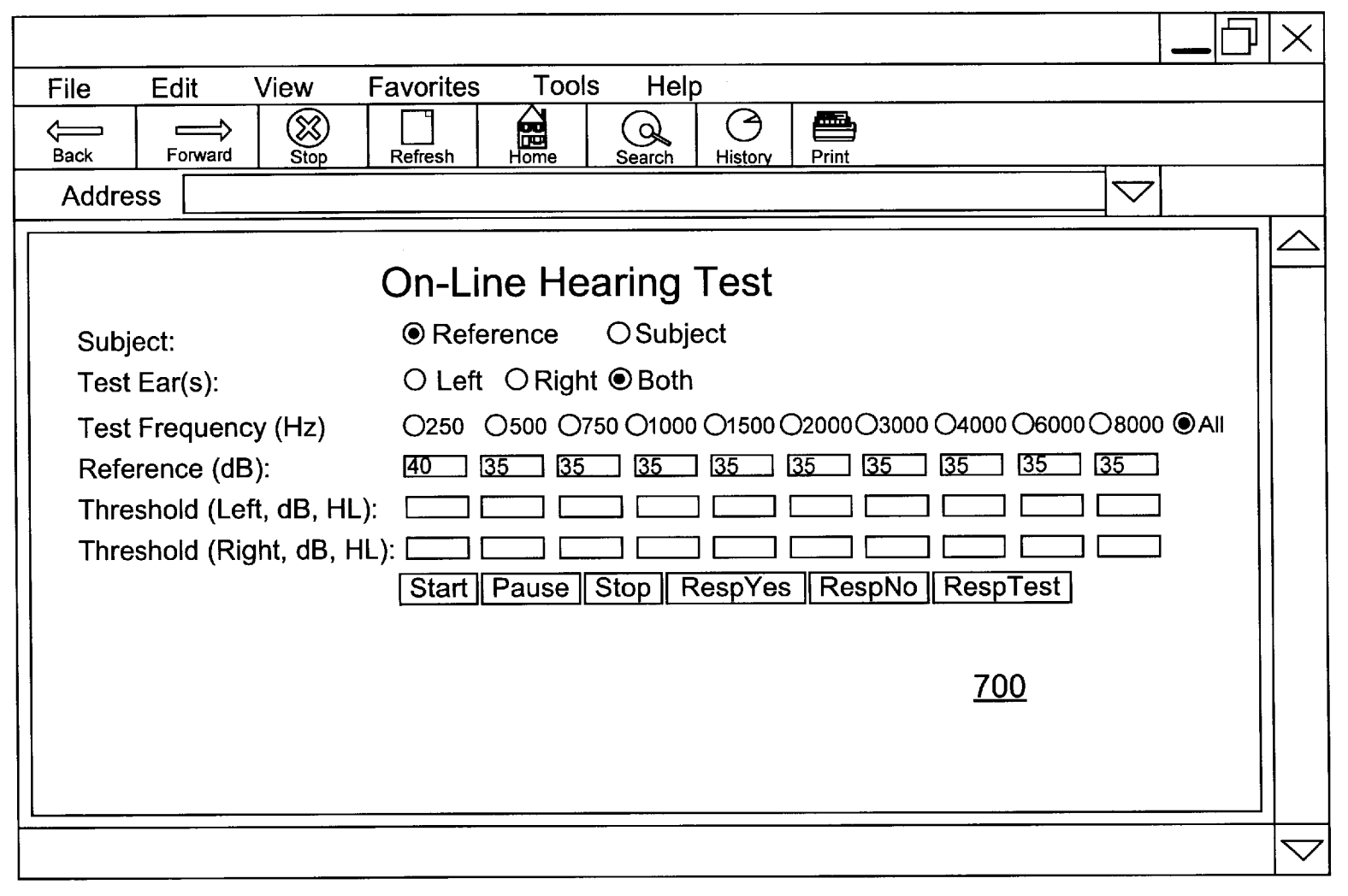

FIG. 7 is a screen depiction of a user interface for a local machine. In this example, a network browser (i.e., Microsoft Internet Explorer) displays a screen that allows a subject to take an on-line hearing test as well as display results of the on-line hearing test. The screen 700 indicates various test frequencies on which the hearing test is performed, the ear to be tested, whether the subject is a reference subject or a target subject. As shown, for each of the test frequencies, a reference in decibels is determined using the reference subject, and threshold hearing levels for left and right ears are determined for the target subject. The screen 700 also illustrates several buttons to allow a user to control the on-line hearing test. Typically, the sound will be coming from the server to the client where it is played on speakers or a headset to the user. The screen 700 depicts a start button to start the on-line hearing test, a pause button to pause the on-line hearing test, a stop button to stop the on-line hearing test, a response yes button (RespYes), a response no button (RespNo), and a reset test button (ResetTest).

Figure 8:
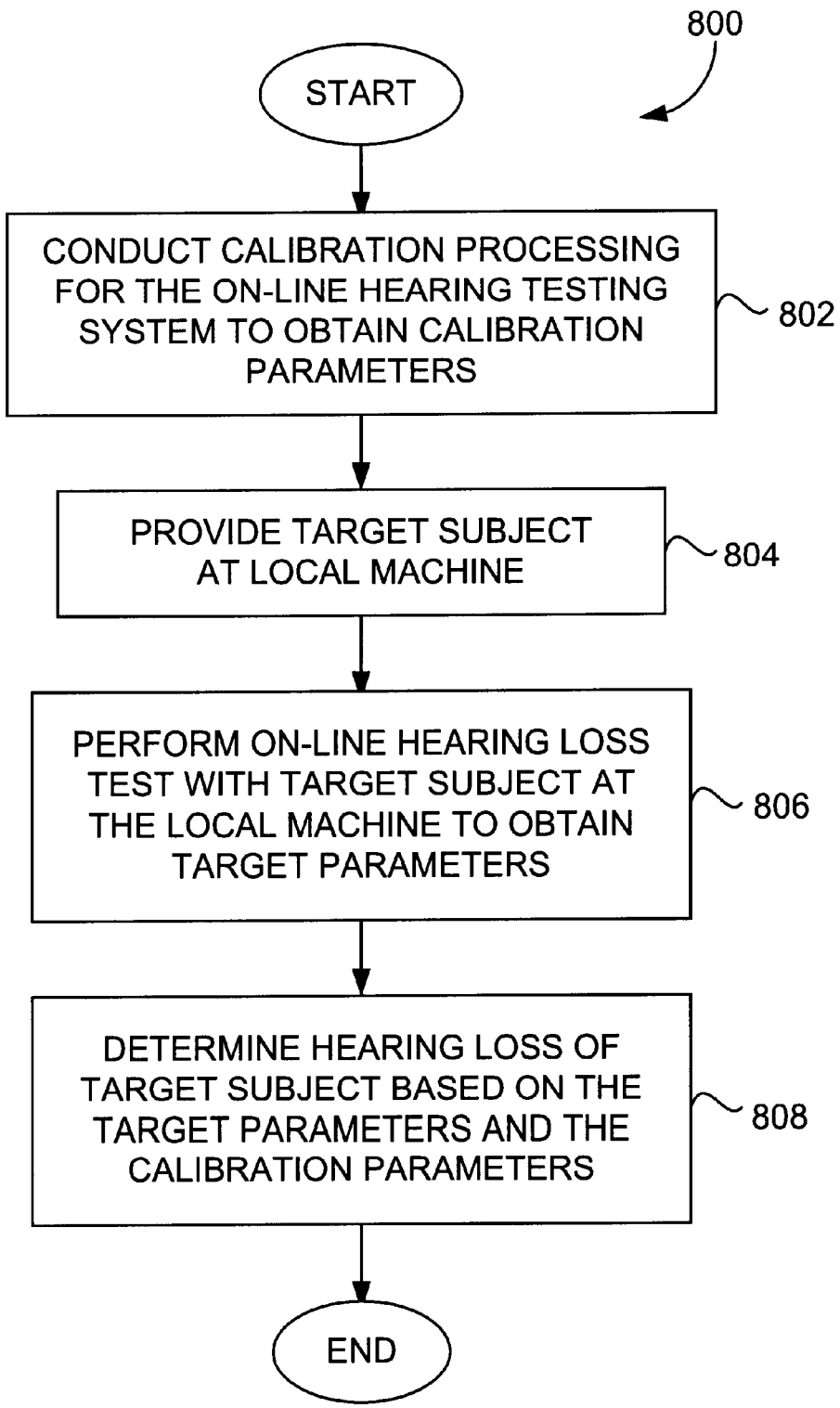
FIG. 8 is a block diagram of calibration-based hearing loss evaluation processing according to one embodiment of the invention.

Although the relative hearing loss evaluation processing 200 shown in FIG. 2 and the reference subject hearing loss processing 300 shown in FIG. 3 make use of a reference subject, other embodiments can provide hearing loss diagnosis without using a reference subject. FIG. 8 is a block diagram of calibration-based hearing loss evaluation processing 800 according to one embodiment of the invention. The calibration-based hearing loss evaluation processing 800 calibrates a sound generating device instead of relying on a reference subject.

The calibration-based hearing loss evaluation processing 800 initially conducts 802 calibration processing for an on-line hearing testing system to obtain calibration parameters. The on-line hearing testing system is, for example, the network-based hearing evaluation and compensation system 100 illustrated in FIG. 1, namely, the local machine 108 thereof. After the calibration parameters have been determined, a target subject is provided 804 at a local machine. The local machine is, for example, a personal computer having a network browser thereon. Next, an on-line hearing loss test is performed 806 with the target reference subject at the local machine. As noted above, the particulars of hearing loss tests, such as tone frequency and amplitude, are generally well known in the art. However, according to the invention, the hearing loss test is performed on-line. As an example, the on-line hearing loss test can be controlled by the hearing assistant server 104 illustrated in FIG. 1 such that the target subject positioned proximate to the local machine 106 or 108 can receive sound signals associated with the hearing loss test and respond them at the local machine. The on-line hearing loss test establishes target parameters. In one embodiment, the target parameters are hearing loss levels. Thereafter, hearing loss of the target subject can be determined 808 based on the target parameters and the calibration parameters. In one embodiment, the hearing loss is expressed as various hearing thresholds for different frequencies. After the hearing loss has been determined 808, the calibration-based hearing loss evaluation processing 800 ends. Note that the calibration-based hearing loss evaluation processing 800 does not require any special purpose hardware, merely a local machine (e.g., personal computer having a network browser with access to a data network) and an audio component (e.g., sound card and speaker).

Figure 9:
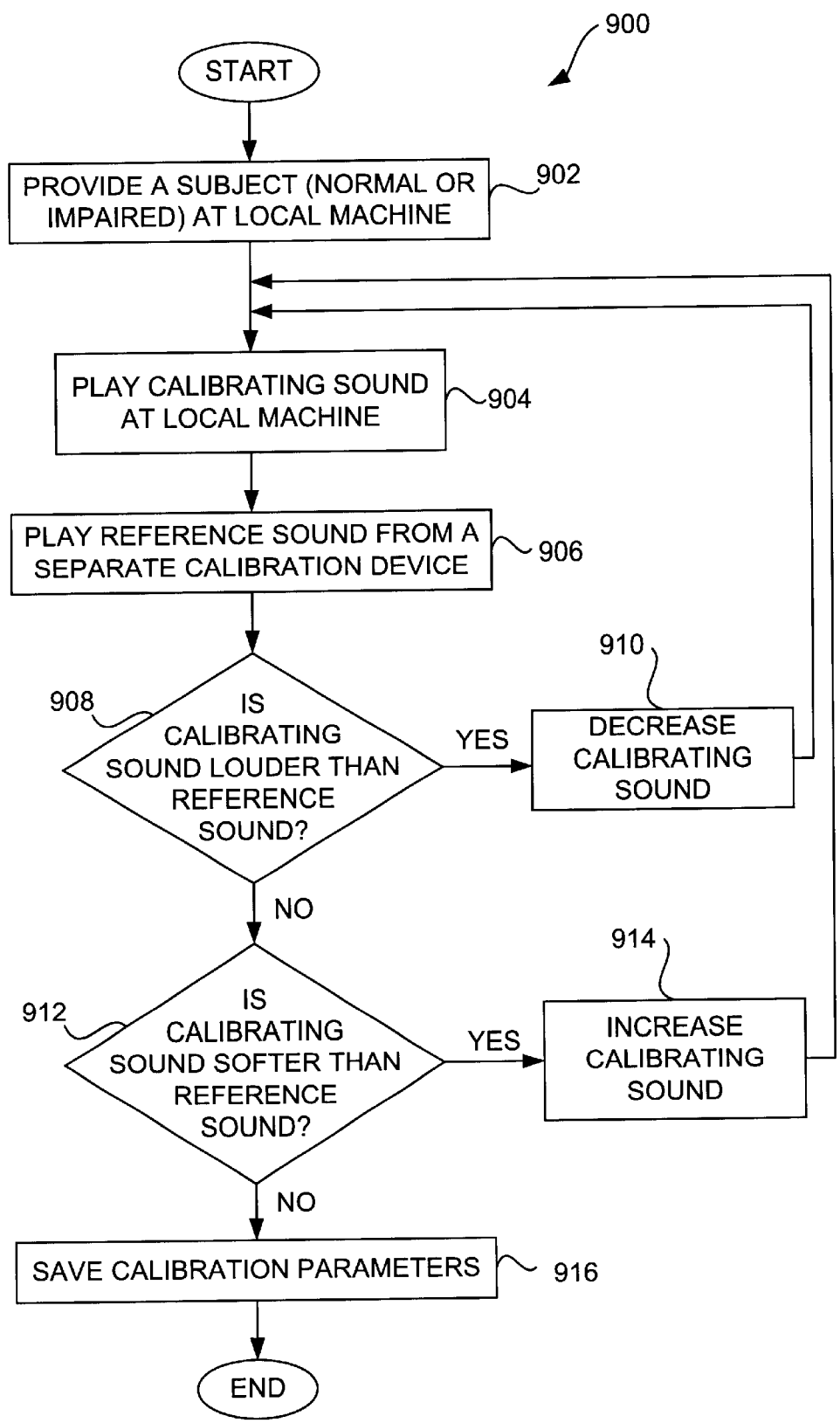
FIG. 9 is a flow diagram of calibration processing according to one embodiment of the invention.

FIG. 9 is a flow diagram of calibration processing 900 according to one embodiment of the invention. The calibration processing 900 is, for example, performed by the calibration processing of operation 802 in FIG. 8. Initially, a subject is provided 902 at the local machine. The subject can have normal or impaired hearing. Next, a calibration sound is played 904 at the local machine. At the same time, a reference sound is played 906 from a calibration device. Typically, the calibration device is separate from the local machine and serves to produce the reference sound. The reference sounds produced by the calibration device are known. As an example, a calibration device can generate a reference sound (e.g., a pure tone) at certain levels and have an on-off mechanism. Further, since for accurate calibration, the calibration device has to be used in a manner such that sound level at the subject's ears is known. Namely, in one implementation, the subject can be instructed to hold the calibration device one (1) foot in front of one's nose. The calibration device can be a special purpose device designed for the very purpose of generating the reference sound. Alternatively, the calibration object could be any object capable of reliably emitting a sound at a substantially known level.

Once the calibrating sound and the reference sound are played 904 and 906, a decision 908 determines whether the calibrating sound is louder to the subject that the reference sound. If the decision 908 determines that the calibrating sound is louder than the reference sound, then the calibrating sound is decreased 910. Alternatively, when the decision 908 determines that the calibrating sound is not louder than the reference sound, then a decision 912 determines whether the calibrating sound is softer than the reference sound. When the decision determines that the calibrating sound is softer than the reference sound, then the calibrating sound is increased 914. Such adjustments to the sound can be achieved in a variety of ways, such as speaker volume control, volume control displayed on a graphical user interface, or software control. Following the decreasing 910 or the increasing 914 to the calibrating sound, the calibration processing 900 returns to repeat the operation 904 and subsequent operations. On the other hand, once the decision determines that the calibrating sound is not softer than the reference sound, the calibration parameters have been determined. Hence, the calibration parameters are saved 916 and the calibration processing 900 is complete and ends.

The invention is preferably implemented in software, but can be implemented in hardware or a combination of hardware and software. The invention can also be embodied as computer readable code on a computer readable medium. The computer readable medium is any data storage device that can store data which can be thereafter be read by a computer system. Examples of the computer readable medium include read-only memory, random-access memory, CD-ROMs, magnetic tape, optical data storage devices, carrier waves. The computer readable medium can also be distributed over a network coupled computer systems so that the computer readable code is stored and executed in a distributed fashion.

The advantages of the invention are numerous. Different embodiments or implementations may yield one or more of the following advantages. One advantage of the invention is that hearing tests are able to be performed on-line. Another advantage of the invention is that no expensive specialized equipment or personnel is needed for performing hearing tests. Another advantage of the invention is that near real-time sound customization can be performed. Still another advantage of the invention is that on-line simulation of hearing aid processing can be performed. Such on-line simulation can include deriving a set of fitting parameters from an on-line diagnosis and then playing back compensated sound. Yet another advantage of the invention is that once hearing loss is diagnosed, proper hearing aids can be recommended and/or purchased on-line, and/or referrals can be made to suitable service or product providers. Still yet another advantage of the invention is that the data obtained from the hearing tests can be archived for later usage or forwarded to suitable service or product providers.

The many features and advantages of the present invention are apparent from the written description and, thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

What is claimed is:

1. A method for determining an amount of hearing loss for a participating subject, said method comprising the acts of:
   (a) performing a first on-line hearing loss test for a reference subject to produce reference parameters;
   (b) performing a second on-line hearing loss test for the participating subject to produce participant parameters; and
   (c) determining relative hearing loss for the participating subject based on the participant parameters and the reference parameters.

2. A method as recited in claim 1, wherein said method further comprises:
   (d) providing a hearing loss report to the participating subject in accordance with the relative hearing loss.

3. A method as recited in claim 1, wherein said performing (a) and (b) of the first and second on-line hearing loss tests are performed on a local machine.

4. A method as recited in claim 3, wherein the local machine is a computing device.

5. A method as recited in claim 3, wherein the local machine is a personal computer.

6. A method as recited in claim 1, wherein said determining (c) of the relative hearing loss is performed at a web server, and wherein the local machine communicates with web server over a data network.

7. A method as recited in claim 6, wherein the data network is the Internet.

8. A method as recited in claim 1, wherein said performing (a) and (b) of the first and second on-line hearing loss tests are performed on a local machine but controlled by the web server.

9. A method as recited in claim 1, wherein said method further comprises:
   (d) informing the participating subject that they suffer from a hearing impairment based on the relative hearing loss.

10. A method as recited in claim 1, wherein said method further comprises:
    (d) recommending on-line that the participating subject obtain a hearing assistance device when the relative hearing loss indicates a significant hearing impairment.

11. A method as recited in claim 10, wherein said method further comprises:
    (e) simulating enhanced hearing of the hearing assistance device to the participating subject.

12. A method as recited in claim 11, wherein said simulating (e) is on-line simulating.

13. A method as recited in claim 1, wherein said method further comprises:
    (d) presenting a list of available hearing aid types to the participating subject when the relative hearing loss indicates a significant hearing impairment.

14. A method as recited in claim 13, wherein said method further comprises:
    (e) simulating a selected one of the available hearing aid types to the participating subject.

15. A method as recited in claim 14, wherein said simulating (e) is on-line simulating.

16. A method as recited in claim 14, wherein said simulating (e) allows the participating subject to adjust parameters associated with the selected one of the available hearing aid types.

17. A method as recited in claim 1, wherein said method further comprises:
    (d) simulating hearing impairment of the participating subject to another subject in accordance with the relative hearing loss of the participating subject.

18. A method as recited in claim 17, wherein said simulating (d) is on-line simulating.

19. A method as recited in claim 1, wherein said method further comprises:
    (d) simulating enhanced hearing to the participating subject, the enhanced hearing compensating for the relative hearing loss of the participating subject.

20. A method as recited in claim 19, wherein said simulating (d) is on-line simulating.

21. A method as recited in claim 1, wherein said method further comprises:
    (d) computerized simulating of a plurality of hearing assistance devices which enhance hearing to the participating subject by compensating for the relative hearing loss of the participating subject.

22. A method as recited in claim 21, wherein said method further comprises:
    (e) ranking the hearing assistance devices examined during said computerized simulating (d).

23. A method as recited in claim 1, wherein said method further comprises:
    (d) referring on-line the participating subject to a hearing aid product or service provider.

24. A method as recited in claim 1, wherein said method further comprises:
    (d) comparing the relative hearing loss with an impairment threshold; and
    (e) referring on-line the participating subject to a hearing aid product or service provider when said comparing (d) indicates that the relative hearing loss exceeds the impairment threshold.

25. A method as recited in claim 1, wherein said method further comprises:
    (d) comparing the relative hearing loss with an impairment threshold; and
    (e) recommending a hearing aid product or service provider when said comparing (d) indicates that the relative hearing loss exceeds the impairment threshold.

26. A method as recited in claim 1, wherein said method further comprises:
    (d) comparing the relative hearing loss with an impairment threshold; and
    (e) on-line simulating enhanced hearing of a hearing assistance device to the participating subject when said comparing (d) indicates that the relative hearing loss exceeds the impairment threshold.

27. An on-line method for providing hearing aid processing, said on-line method comprising the acts of:
    performing an on-line diagnosis of a user's hearing loss;
    determining hearing aid parameters based on the on-line diagnosis;
    modifying an electronic sound source based on the hearing aid parameters to produce a modified electronic sound source; and
    playing the modified electronic sound source for the user.

28. An on-line method as recited in claim 27, wherein the electronic sound source is provided at a web server, and wherein said performing of the on-line diagnosis uses at least a local computer at the user's location.

29. An on-line method as recited in claim 28, wherein said performing of the on-line diagnosis includes at least transmitting predetermined sound signal to the user's computer over a data network.

30. An on-line method as recited in claim 27, wherein said playing comprises:

transmitting the modified electronic sound source to a local computer at the user's location over a data network; and playing the modified electronic sound source at the local machine.

31. An on-line method for providing hearing aid processing, said on-line method comprising the acts of:

receiving hearing loss data on-line for a user;

determining hearing aid parameters based on the hearing loss data;

modifying an electronic sound source based on the hearing aid parameters to produce a modified electronic sound source; and playing the modified electronic sound source for the user.

32. A method as recited in claim 31, wherein said method further comprises the act of:

allowing on-line adjustment to the hearing aid parameters by the user.

33. An on-line method as recited in claim 31, wherein said playing comprises:

transmitting the modified electronic sound source to a local computer at the user's location over a data network; and playing the modified electronic sound source at the local machine.

34. A method for referring a hearing impaired listener to a hearing product or service specialist, said method comprising the acts of:

receiving hearing loss data on-line for a hearing impaired user;

receiving a selection of one of a plurality of hearing product or service providers;

directing the hearing impaired listener to the selected one of the hearing product or service providers; and forwarding the hearing loss data for the hearing impaired listener to the selected one of the hearing product or service providers over a data network.

35. A method as recited in claim 34, wherein said method further comprises the act of:

scheduling an appointment on-line with the selected one of the hearing product or service providers for the hearing impaired listener.

36. A method as recited in claim 34, wherein said method further comprises the act of:

simulating enhanced hearing for the hearing impaired listener, the enhanced hearing compensates for the determined hearing loss of the hearing impaired listener.

37. A method as recited in claim 34, wherein said receiving of the hearing loss data comprises:

determining hearing loss of the hearing impaired listener on-line, the hearing loss being represented in the hearing loss data.

38. A method as recited in claim 37, wherein said method further comprises the act of:

scheduling an appointment on-line with the selected one of the hearing product or service providers for the hearing impaired listener.

39. A method as recited in claim 37, wherein said method further comprises the act of:

simulating enhanced hearing for the hearing impaired listener, the enhanced hearing compensates for the determined hearing loss of the hearing impaired listener.

40. A method as recited in claim 39, wherein said method further comprises the act of:

purchasing a hearing aid product on-line based on the hearing loss data.

41. A method as recited in claim 34, wherein said method further comprises the act of:

purchasing a hearing aid product on-line based on the hearing loss data.

42. An on-line method for providing impaired hearing simulation, said on-line method comprising the acts of:

receiving hearing loss data on-line for a first user, the first user being hearing impaired;

modifying an electronic sound source based on the hearing less data to produce an impaired electronic sound source; and playing the impaired electronic sound source for a second user, the second user being substantially non-hearing impaired.

43. A computer readable medium including computer program code for determining an amount of hearing loss for a participating subject, said computer readable medium comprising:

computer program code for performing a first on-line hearing loss test for a reference subject to produce reference parameters;

computer program code for performing a second on-line hearing loss test for the participating subject to produce participant parameters; and computer program code for determining relative hearing loss for the participating subject based on the participant parameters and the reference parameters.

44. A computer readable medium including computer program code for providing on-line hearing aid processing, said computer readable medium comprising:

computer program code for accessing an on-line diagnosis of a user's hearing loss;

computer program code for determining hearing aid parameters based on the on-line diagnosis;

computer program code for modifying an electronic sound source based on the hearing aid parameters to produce a modified electronic sound source; and computer program code for transmitting the modified electronic sound source for the user.

45. A computer readable medium including computer program code for referring a hearing impaired listener to a hearing product or service specialist, said computer readable medium comprising:

computer program code for determining hearing loss of the hearing impaired listener on-line, the hearing loss being represented in hearing loss data;

computer program code for receiving a selection of one of a plurality of hearing product or service providers;

computer program code for directing the hearing impaired listener the selected one of the hearing product or service providers; and computer program code for forwarding the hearing loss data for the hearing impaired listener to the selected one of the hearing product or service providers over a data network.

* * * * *